United States Patent
Igarashi

(10) Patent No.: US 10,844,176 B2
(45) Date of Patent: Nov. 24, 2020

(54) MANUFACTURING METHOD OF SILICONE RUBBER PARTICLE-DISPERSED EMULSION

(71) Applicant: Wacker Chemie AG, Munich (DE)

(72) Inventor: Kenji Igarashi, Chikusei (JP)

(73) Assignee: WACKER CHEMIE AG, Munich (DE)

( * ) Notice: Subject to any disclaimer, the term of this patent is extended or adjusted under 35 U.S.C. 154(b) by 79 days.

(21) Appl. No.: 16/076,892

(22) PCT Filed: Feb. 16, 2017

(86) PCT No.: PCT/EP2017/053561
§ 371 (c)(1),
(2) Date: Aug. 9, 2018

(87) PCT Pub. No.: WO2017/140816
PCT Pub. Date: Aug. 24, 2017

(65) Prior Publication Data
US 2019/0055362 A1 Feb. 21, 2019

(30) Foreign Application Priority Data
Feb. 19, 2016 (JP) .................. 2016-029721

(51) Int. Cl.
| C08G 77/08 | (2006.01) |
| A61Q 19/00 | (2006.01) |
| A61K 8/895 | (2006.01) |
| A61K 8/06 | (2006.01) |
| C08G 77/12 | (2006.01) |
| C08G 77/20 | (2006.01) |
| A61K 8/64 | (2006.01) |
| C08G 77/06 | (2006.01) |
| C08K 5/17 | (2006.01) |
| C08K 5/56 | (2006.01) |
| C08L 83/04 | (2006.01) |
| C08L 83/14 | (2006.01) |

(52) U.S. Cl.
CPC .............. *C08G 77/08* (2013.01); *A61K 8/062* (2013.01); *A61K 8/64* (2013.01); *A61K 8/895* (2013.01); *A61Q 19/00* (2013.01); *C08G 77/06* (2013.01); *C08G 77/12* (2013.01); *C08G 77/20* (2013.01); *C08K 5/175* (2013.01); *C08K 5/56* (2013.01); *C08L 83/04* (2013.01); *C08L 83/14* (2013.01); *A61K 2800/10* (2013.01)

(58) Field of Classification Search
CPC ........ C08G 77/12; C08G 77/20; C08G 77/08; A01N 25/04; A61K 8/891
See application file for complete search history.

(56) References Cited

U.S. PATENT DOCUMENTS

2002/0187904 A1 12/2002 Perron et al.
2014/0335044 A1 11/2014 Inokuchi et al.

FOREIGN PATENT DOCUMENTS

| CN | 104140684 A | 11/2014 |
| EP | 1245224 A1 | 10/2002 |
| EP | 2556818 A1 | 2/2013 |
| EP | 2581415 A1 | 4/2013 |
| JP | 63309565 A | 12/1988 |
| JP | 11140191 A | 5/1999 |
| JP | 11140191 * | 9/1999 |

OTHER PUBLICATIONS

JP 11 140191 machine translation (1999).*

* cited by examiner

*Primary Examiner* — Kuo Liang Peng
(74) *Attorney, Agent, or Firm* — Brooks Kushman P.C.

(57) ABSTRACT

The use of an N-acylaminoacid condensate as a surfactant in the preparation of silicone rubber particle emulsions allows the emulsions to be prepared with exceptionally low levels of surfactants. The resulting rubber particles display typical silicone rubber characteristics in contrast to rubber particles prepared using larger amounts of conventional surfactants.

5 Claims, No Drawings

MANUFACTURING METHOD OF SILICONE RUBBER PARTICLE-DISPERSED EMULSION

CROSS REFERENCE TO RELATED APPLICATIONS

This application is the U.S. National Phase of PCT Appln. No. PCT/EP2017/053561 filed Feb. 16, 2017, which claims priority to Japanese Application No. 2016-029721 filed Feb. 19, 2016, the disclosures of which are incorporated in their entirety by reference herein.

BACKGROUND OF THE INVENTION

1. Field of the Invention

The present invention relates to a manufacturing method of a silicone rubber particle-dispersed emulsion which does not cause an environmental problem attributable to a conventional organic surfactant component, does not decrease dispersion stability in the emulsion, and does not adversely affect the intrinsic characteristics of silicone.

2. Description of the Related Art

Silicone rubber particles, which have high viscoelasticity, light scattering, transmittance, and oil absorbing properties based on the large surface area thereof, are widely used in industrial fields, such as cosmetics, synthetic resin materials, and synthetic rubber materials. As a major trend in recent years, the silicone rubber particles, which are materials for the purposes of environmental preservation and safety improvement, are manufactured as an emulsion, that is, dispersed in water, in general industrial applications. However, silicone has hydrophobic properties, which has caused a problem in that dispersibility is low.

Therefore, an emulsion of silicone rubber particles with an organic nonionic surfactant is proposed as described in Japanese laid open application S63-309565. However, the concentration of the silicone rubber particles was low, and stability was still insufficient.

Therefore, Japanese laid open application H11-140191 discloses an emulsion of silicone rubber particles which are stabilized by using a combination of 0.1% by mass or more of an organic nonionic surfactant and 0.01% by mass or more of an organic ionic surfactant. Thus, the organic surfactants are indispensably used in an amount of at least 0.11% by mass or more in the composition. In a practical use, the surfactants are required to be used in an amount of approximately 1.0% in most cases in consideration of the dispersion stability of the composition.

However, according to various recent studies concerning the influence on aquatic organisms or the like, the organic surfactant components are reported to adversely affect aquatic organisms even at an extremely low concentration. Thus, it is desired to suppress the release of the organic surfactant components into the environment as low as possible.

Also, in "7.3.2 Irritation and corrosion" of "CERI Hazard Assessment Report, poly(oxyethylene) alkyl ether (only poly(oxyethylene) alkyl ether including an alkyl group having 12 to 15 carbon atoms, and a mixture thereof)" by Chemicals Evaluation and Research Institute, Japan, it is described that polyoxyethylene alkyl ethers, which are often used when manufacturing silicone rubber particles for the cosmetics application, cause irritation to skin and eyes with an amount of 0.1 parts by mass or more.

Furthermore, common organic surfactant components are concentrated during drying processes, thereby developing a liquid crystal phase having a high viscosity, even when the added amount thereof in 100 parts by mass of an emulsion is approximately 0.5 parts by mass. This inhibits low friction which is intrinsically expressed by silicone rubber particles.

For example, when a common organic surfactant component is added in cosmetics or the like, the development of a liquid crystal phase causes a viscosity increase, leading to undesired senses of tack and friction. As a result, there has been a problem in which the hydrophobic properties expected in silicone particles and the favorable senses of touch derived from low surface tension are decreased.

Furthermore, the formation of a liquid crystal layer attributable to an organic surfactant on the surface of silicone particles means that a free organic surfactant which is not adsorbed to the particles is dissolved into an aqueous phase. Accordingly, it is not preferable in terms of the environmental preservation that an organic surfactant be used in an amount of approximately 0.5 parts by mass or more in 100 parts by mass of an emulsion.

Also, examples of surfactant components which are most commonly used in this technical field may include an alkyl polyether where the alkyl group has 12 to 15 carbon atoms. This type of surfactant is designated as a chemical which could adversely affect the environment, and the emission thereof is regulated according to PRTR (Pollutant Release and Transfer Register). Thus, the use thereof has recently been limited.

Technical Problem

It would be desirable to limit the amount of an organic surfactant contained in 100 parts by mass of an emulsion to less than 0.1% by mass so that the intrinsic characteristics of silicone rubber particles are exerted without adversely affecting the environment and the health. However, none of the conventional techniques have disclosed a specific method for achieving such an object without decreasing the dispersion stability of the emulsion. The present invention has been achieved in view of the problems described above.

SUMMARY OF THE INVENTION

The present invention provides a manufacturing method for a silicone rubber particle-dispersed emulsion which does not cause an environmental problem attributable to a conventional organic surfactant component, does not decrease dispersion stability in an emulsion, and exerts intrinsic characteristics of silicone rubber particles, by providing a silicone rubber particle-dispersed emulsion having favorable storage stability by a method including: dispersing an alkenyl group-containing organopolysiloxane and an organohydrogen polysiloxane in water with an organic surfactant in an amount of less than 0.1 parts by mass with respect to 100 parts by mass of the emulsion, which is an amount that does not cause an environmental problem and does not inhibit the senses of touch specific to silicone rubber particles; and thereafter allowing an addition curing reaction to proceed by a hydrosilylation reaction with a platinum catalyst. The silicone rubber particle the have the intrinsic characteristics of silicone rubber.

DETAILED DESCRIPTION OF THE PREFERRED EMBODIMENTS

The present invention has been achieved on the basis of the above-described knowledge. That is, the inventive manufacturing method for a silicone rubber particle-dispersed emulsion includes:

preparing an oil-in-water emulsion by using
a component (A) which is an organic surfactant in an amount of less than 0.1 parts by mass, and
a component (B) including 20 to 80 parts by mass of an organopolysiloxane containing an alkenyl group-containing organopolysiloxane defined by a component (I) described below, and an organohydrogen polysiloxane defined by a component (II) described below, such that 0.05 to 59.05 parts by mass of the component (II) are contained relative to 19.95 to 79.95 parts by mass of the component (I), wherein
the component (I) is an alkenyl group-containing organopolysiloxane having an average composition formula represented by the general formula (1) and containing two or more alkenyl groups bonded to a silicon atom in one molecule,

where
$R^1$ each individually is a monovalent hydrocarbon group which does not contain an aliphatic unsaturated group,
$R^2$ is an alkenyl group,
a is 0.999 to 2.999,
b is 0.001 to 2, and
a+b is 1 to 3,
the component (II) is an organohydrogen polysiloxane having an average composition formula represented by the general formula (2) and containing two or more hydrogen atoms bonded to a silicon atom in one molecule,

where in the formula (2),
$R^3$ each individually is a monovalent hydrocarbon group which does not contain an aliphatic unsaturated group,
c is 0.999 to 2.999,
d is 0.001 to 2, and
c+d is 1 to 3; and
adding, to the resulting oil-in-water emulsion, a component (C) which is a platinum group-based metal-containing addition catalyst in an amount of 1 to 5,000 ppm relative to the total amount of the components (I) and (II).

The manufacturing method for the silicone rubber particle-dispersed emulsion according to the present invention can reduce the amount of commonly used organic nonionic, anionic, cationic or amphoteric surfactans (emulsifiers) to less than 0.1% by mass. Thus, the intrinsic characteristics of the silicone rubber particles, such as the decrease in frictional forces and tack, can be maintained without adversely affecting the environment and the health and also without decreasing the dispersibility of the emulsion.

The manufacturing method for a silicone rubber particle-dispersed emulsion according to the present invention will be described in detail below.

The manufacture of the silicone rubber particle-dispersed emulsion according to the present invention is achieved by selecting and using a compound or a substance having an emulsifying action which has not been possessed by a conventional organic surfactant. Examples of such a compound or substance may include, but are not limited to, an ionic compound, and a substance exhibiting an emulsifying action similar to that of an organic surfactant.

With the above-described surfactant as the component (A), the components (I) and (II) as the component (B) are dispersed in water, thereby to obtain an oil-in-water emulsion. The platinum group-based metal-containing addition catalyst as the component (C) is added to the obtained emulsion to allow the components (I) and (II) to be reacted and cured. Thus, silicone rubber particles are obtained.

The rubber elasticity of the silicone rubber particles obtained by the manufacturing method according to the present invention falls within the range of 5 to 95 based on Shore A.

Component (A)

The component (A) is an organic surfactant which emulsifies the components (I) and (II) as the component (B). The component (A) is a compound or a substance having an emulsifying action in a use amount of less than 0.1% by mass. This use amount has not been realized by a conventional organic surfactant. Examples thereof may include, but are not limited to, ionic compounds. Also, two or more of these surfactants may be used in combination.

The amount of the component (A) is not limited as long as it is less than 0.1% by mass in total.

As the component (A), an N-acyl amino acid condensate is preferable.

The N-acyl amino acid condensate is obtained by condensing an N-acylated product of an acidic amino acid represented by the general formula (3) described below.

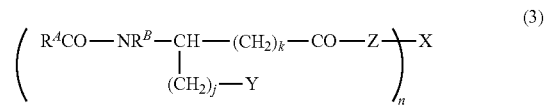

In the general formula (3), $R^A$ is a hydrocarbon group having 1 to 23 carbon atoms, and $R^A CO$ indicates a long-chain acyl group derived from a saturated or unsaturated fatty acid having 2 to 20 carbon atoms. $R^A$ is preferably a hydrocarbon group having 7 to 17 carbon atoms. $R^A$ may be any of a straight chain, a branched chain, a cyclic chain, or an aromatic hydrocarbon chain, and may have a substituent group. $R^A CO—$ is preferably a derivative from a saturated or unsaturated fatty acid having 8 to 20 carbon atoms. Specific examples thereof may include lauric acid, myristic acid, and stearic acid.

In the general formula (3), $R^B$ is a hydrogen atom or a hydrocarbon group having 1 to 3 carbon atoms, and may have a carboxyl group or a sulfonic acid group. Specific examples of the hydrocarbon group having 1 to 3 carbon atoms may include a methyl group, an ethyl group, a propyl group, an isopropyl group, a hydroxymethyl group, a hydroxyethyl group, a hydroxy(iso)propyl group, a dihydroxy(iso)propyl group, a carboxymethyl group, a carboxyethyl group, a carboxypropyl group and a sulfoethyl group. $R^B$ is preferably a hydrogen atom.

In the general formula (3), Y is a carboxyl group, a sulfonic acid group, a sulfuric acid ester group, a phosphoric acid ester group, or a salt thereof, and preferably a carboxyl group or a salt thereof.

Examples of a basic substance which forms a salt with Y as an acid group may include metals such as alkali metals, and organic basic substances. Examples of the alkali metals include sodium, potassium, and lithium. Examples of alkaline earth metals include calcium and magnesium. Examples of metals other than the above-described metals, which can form a salt, may include aluminum, zinc, iron, cobalt, titanium, zirconium, and silver. Examples of the organic basic substances may include, but are not particularly limited to, an organic amine salt and a basic amino acid salt. Examples of the organic amine salt may include salts of ammonia, monoethanolamine, diethanolamine, triethanolamine, and triisopropanolamine. Examples of the basic amino acid salts may include salts of arginine and lysine. Other examples may include an ammonium salt and a polyvalent metal salt. Also, in the general formula (3), Y may contain one salt or two or more salts arbitrarily selected from the above-described salts.

In the general formula (3), Z is a linking group which varies dependent on the compound for condensing the N-acyl amino acid derivative, and is —NR'— (R' is a hydrogen atom or a hydrocarbon group having 1 to 10 carbon atoms), —O—, or —S—. In the general formula (3), j and k are each any of 0, 1 and 2, and are not simultaneously 0, and n is 2 or more. Preferably n is 2 to 10. Specific examples of the amino acid that constitutes the N-acyl amino acid include glutamic acid and aspartic acid, preferably glutamic acid.

X in the general formula (3) is a group for condensing the N-acyl amino acid derivative in the general formula (3), and is a compound with a molecular weight of 1,000,000 or less which has two or more functional groups for contributing to a condensation reaction with a carboxyl group of the N-acyl amino acid derivative. The functional group for contributing to condensation is preferably one or two or more selected from a hydroxyl group, an amino group, and a thiol group. Specific examples of the compound used for the condensation of the N-acyl amino acid derivative may include amino acids having two amino groups or having a hydroxyl group or a thiol group with an amino group, such as arginine, lysine, tyrosine, and tryptophan; compounds having an amino group and a hydroxyl group in the molecule, such as aminopropanol, aminophenol, and glucosamine; compounds having a thiol group and a hydroxyl group in a molecule, such as mercaptopropanediol; compounds having a thiol group and an amino group, such as aminothiophenol; protein or peptide, or a hydrolysate thereof; and a polyhydroxyl compound. Among these, a product obtained by condensation with an amino acid is preferable, and lysine is preferable. Specific examples of a lysine condensate of the N-acyl-glutamic acid derivative may include sodium dilauramidoglutamide lysine commercially available as Pellicer (trademark) from Asahi Kasei Chemicals Corporation.

As the component (A), a conventional organic surfactant may be used in combination, as long as the total amount of the organic surfactants is less than 0.1 parts by mass.

In particular, a nonionic surfactant which is unlikely to cause irritation to skin is suitable. Examples thereof may include polyoxyalkylene alkyl ethers, such as polyoxyethylene tridecyl ether, polyoxyethylene hexadecyl ether, and polyoxyethylene octadecyl ether, polyoxyethylene hydrogenated castor oil, and polyoxyethylene sorbitan acid ester.

The amount of the surfactants as the component (A) is preferably less than 0.07 parts by mass in the emulsion.

This is because the smooth sense of touch intrinsically expressed by silicone particles decreases when the amount is 0.07 parts by mass or more.

The component (A) according to the present invention may contain an inorganic filler, such as titanium oxide, talc, zinc oxide, precipitated barium sulfate, silica, and carbon black, as long as the object of the present invention is not impaired.

The component (I) is an organopolysiloxane having an average compositional formula represented by the general formula (1) and containing two or more alkenyl groups bonded to silicon in one molecule. The alkenyl group-containing organopolysiloxane as the component (I) is also referred to as an alkenyl organopolysiloxane below:

$$R^1_a R^2_b SiO_{(4-a-b)/2} \tag{1}$$

In the formula (1), $R^1$ is a monovalent hydrocarbon group which does not contain an aliphatic unsaturated group, $R^2$ is an alkenyl group, a is 0.999 to 2.999, b is 0.001 to 2, and a+b is 1 to 3.

In the formula (1), $R^1$ preferably has 1 to 18 carbon atoms. Also, $R^1$ preferably forms an SiC— bond. Furthermore, $R^1$ is preferably a substituted or unsubstituted hydrocarbon group which does not have an aliphatic carbon-carbon multiple bond.

In the formula (1), $R^2$ preferably has 1 to 18 carbon atoms. $R^2$ is preferably a monovalent hydrocarbon group having an aliphatic carbon-carbon multiple bond. The alkenyl organopolysiloxane represented by the general formula (1) has at least two or more $R^2$s in average per molecule.

Examples of the alkenyl group in the component (I) may include an alkenyl group having 2 to 8 carbon atoms, such as a vinyl group, an allyl group, a 1-butenyl group, and a 1-hexenyl group. The alkenyl group is preferably a vinyl group or an allyl group, and more preferably a vinyl group. These alkenyl groups react with an organohydrogen polysiloxane as the component (II) described later to form a crosslinked structure. The number of alkenyl groups contained in one molecule of the component (I) is preferably two or more. Such alkenyl groups may be bonded to a silicon atom at the termini of the molecular chain, or may be bonded to a silicon atom in the molecular chain. From the viewpoint of curing reaction rates, the alkenyl group-containing polyorganosiloxane in which alkenyl groups are bonded to only a silicon atom at the termini of the molecular chain is preferable.

Other organic groups bonded to the silicon atom in the component (I) are preferably substituted or unsubstituted monovalent hydrocarbon groups which have 1 to 12 carbon atoms and which do not contain an aliphatic unsaturated bond. Examples of the other organic groups include an alkyl group such as a methyl group, an ethyl group, a propyl group, an isopropyl group, a butyl group, an isobutyl group, a t-butyl group, a pentyl group, a neopentyl group, a hexyl group, a 2-ethylhexyl group, a heptyl group, an octyl group, a nonyl group, a decyl group, or a dodecyl group; a cycloalkyl group such as a cyclopentyl group, a cyclohexyl group, or a cycloheptyl group; an aryl group, such as a phenyl group, a tolyl group, a xylyl group, a biphenyl group, or a naphthyl group; an aralkyl group such as a benzyl group, a phenylethyl group, a phenylpropyl group, or a methyl benzyl group; and a substituted hydrocarbon group in which a portion or an entirety of hydrogen atoms in each of these hydrocarbon groups is replaced by a halogen atom, a cyano group, and the like, such as a chloromethyl group, a 2-bromoethyl group, a 3,3,3-trifluoropropyl group, a 3-chloropropyl group, a chlorophenyl group, a dibromophenyl group, a tetrachlorophenyl group, a difluorophenyl group, a β-cyanoethyl group, a γ-cyanopropyl group, or a β-cyanopropyl group. A particularly preferable organic group is a methyl group or a phenyl group.

The component (I) may be a linear and/or branched component or contain a mixture thereof. When a branched alkenyl group-containing polyorganosiloxane is used, the crosslinking density becomes high. Accordingly, a peel force at a low speed becomes large, inhibiting the achievement of low peel force. Therefore, a linear alkenyl group-containing polyorganosiloxane is more preferable. This alkenyl group-containing polyorganosiloxane is manufactured by a method known by a person skilled in the art.

The viscosity at 25° C. of the component (I) is preferably 5 to 2,000,000 mPa·s, more preferably 50 to 100,000 mPa·s, and most preferably 100 to 50,000 mPa·s. When it is less than 5 mPa·s or exceeds 2,000,000 mPa·s, emulsification is inhibited, and a stable aqueous dispersion liquid cannot be obtained. Furthermore, the content of the component (I), in order to obtain the silicone rubber particles, preferably falls within the range of 19.95 to 79.95 parts by mass. When the content is less than 19.95 parts by mass, sufficient emulsifying accuracy is not obtained, and the yield decreases. When the content is more than 79.95 parts by mass, the viscosity of the aqueous emulsion increases, causing handling properties to deteriorate. The content is more preferably 30 to 70 parts by mass.

The alkenyl group-containing polyorganosiloxane as the component (I) can be manufactured by methods known to those skilled in the art, for example by condensation and/or ring-opening polymerization of chain and/or cyclic low-molecular-weight siloxanes with an acid catalyst, such as sulfuric acid, hydrochloric acid, nitric acid, active terra alba, and tris(2-chloroethyl) phosphite, or with a basic catalyst, such as lithium hydroxide, sodium hydroxide, potassium hydroxide, tetramethylammonium hydroxide, tetra-n-butylammonium hydroxide, tetra-n-butylphosphonium hydroxide, sodium silanolate, and potassium silanolate.

Component (II)

An organohydrogen polysiloxane as the component (II) is represented by the average composition formula (2) below:

$$R^3{}_c H_d SiO_{(4-c-d)/2} \qquad (2).$$

In the formula (2), $R^3$ is a monovalent hydrocarbon group which is the same or different and which does not contain an aliphatic unsaturated group, c is 0.999 to 2.999, d is 0.001 to 2, and c+d is 1 to 3. $R^3$ in the formula (2) is the hydrocarbon group indicated above as an example for $R^1$, preferably an alkyl group, and more preferably a methyl group. The number of hydrogen atoms bonded to a silicon atom of the component (II) is preferably two or more in one molecule.

The organohydrogen polysiloxane as the component (II) preferably contains 5% by mass or more of an organohydrogen polysiloxane having hydrogen atoms bonded to the silicon atom in the molecular side chain.

The added amount of the component (II) in the composition according to the present invention depends on the amount of the alkenyl group in the component (I), and is adjusted such that the ratio (NH/NA) between the number (NA) of alkenyl groups bonded to the silicon atom in the component (I) and the number (NH) of hydrogen atoms bonded to the silicon atom contained in the component (II) is 0.8≤(NH/NA)≤2.0, and preferably 0.9≤(NH/NA)≤1.7. When NH/NA is less than 0.8, the curing of the composition does not sufficiently proceed, thereby inhibiting development of the loose sense of touch as the rubber particle. Also, when NH/NA is 2.0 or more, a highly reactive organohydrogen polysiloxane remains in the rubber particle, causing a problem in safety as cosmetic materials.

The organohydrogen polysiloxane as the component (II) is also manufactured by a method known to a person skilled in the art.

The viscosity at 25° C. of the component (II) is preferably 1 to 3,000 mPa·s, and more preferably 1 to 1,500 mPa·s. When it is less than 1 MPa·s, the curing properties are excessively high, resulting in insufficient elasticity obtained. When it is more than 3,000 mPa·s, the reactivity is lowered, resulting in deteriorated curing properties.

Component (C)

The component (C) is a platinum group-based catalyst used as a hydrosilylation catalyst. The platinum group-based catalyst (C) includes a metal or a compound containing the metal. The metal which constitutes the platinum group-based catalyst (C) may be, for example, platinum, rhodium, palladium, ruthenium, or iridium, and preferably platinum. Alternatively, compounds containing these metals may be used. Among these, a platinum-based catalyst is particularly high in reactivity, and therefore suitable. The metal may be fixed to a carrier material (for example, activated carbon, aluminum oxide, or silicon oxide) having a fine particulate shape. Examples of the platinum compounds include platinum halides (for example, a reaction product including $PtCl_4$, $H_2PtCl_4 \cdot 6H_2O$, $Na_2PtCl_4 \cdot 4H_2O$ or $H_2PtCl_4 \cdot 6H_2O$ and cyclohexane), platinum-olefin complexes, platinum-alcohol complexes, platinum-alcoholate complexes, platinum-ether complexes, platinum-aldehyde complexes, platinum-ketone complexes, platinum-vinylsiloxane complexes (for example, a platinum-1,3-divinyl 1,1,3,3-tetramethyldisiloxane complex, bis-(γ-picoline)-platinum dichloride, trimethylene dipyridine-platinum dichloride, dicyclopentadiene-platinum dichloride, cyclooctadiene-platinum dichloride, or cyclopentadiene-platinum dichloride), bis(alkynyl)bis(triphenylphosphine)platinum complexes, and bis(alkynyl) (cyclooctadiene)platinum complexes. Also, the hydrosilylation catalyst may be in the form of microcapsules. In this case, a fine particle solid material which contains a catalyst and is not dissolved in the polyorganosiloxane is, for example, a thermoplastic resin (for example, a polyester resin or a silicone resin). Also, platinum-based catalysts in the form of clathrate compounds can also be used in, for example, cyclodextrin.

The amount of the platinum group-based catalyst as the component (C) to be added for obtaining the silicone rubber particle-dispersed emulsion according to the present invention is preferably such that the amount of the platinum group-based metal with respect to the total weight of the components (I) and (II) of the diorganopolysiloxane as the component (B) is 1 to 5,000 ppm, preferably 5 to 1,000 ppm, and more preferably 20 to 500 ppm. When the content is less than 1 ppm, the curing process takes time, possibly resulting in deteriorated production efficiency. When the content is more than 5,000 ppm, a problem is caused in terms of appearance. For example, the dispersion may be colored brown.

The preparation method of the dispersed emulsion of the silicone rubber particles according to the present invention may be, but is not particularly limited to, known methods. The dispersed emulsion can be prepared by mixing and emulsifying the above-described components using a common mixer suitable for the preparation of an emulsion, such as a homogenizer, a colloid mill, a homomixer, or a high-speed stator rotor stirrer.

As a liquid phase to be contained in the silicone rubber particle dispersion, water is preferable. The water to be used is preferably, but is not particularly limited to, ion exchanged water, and preferably has a pH value of 2 to 12, and more preferably 4 to 10.

The silicone rubber particle-dispersed emulsion according to the present invention may contain, other than water, a hydrophilic component, such as ethanol, 1-propanol, 2-propanol, 1,2-propylene glycol, 1,2-butanediol, 1,3-butanediol, 1,5-pentanediol, 1,2-hexanediol, dipropylene glycol, glycerin, trimethylolpropane, and pentaerythritol, within the range that does not impair the object of the invention.

The silicone rubber particle-dispersed emulsion according to the present invention may contain, as a preservative, salicylic acid, sodium benzoate, sodium dehydroacetate, potassium sorbate, phenoxy ethanol, methyl parahydroxybenzoate, and butyl parahydroxybenzoate, within the range that does not impair the object of the invention. Also, the silicone rubber particle-dispersed emulsion according to the present invention may contain, for example, oil, such as silicone oil as a lubrication component, and liquid paraffin, glycerin and various flavors for other purposes, depending on its application.

The method for isolating the silicone rubber particles from the silicone rubber particle-dispersed emulsion according to the present invention is not limited, and may be any known method. For example, the silicone rubber particles can be obtained by removing water through heating and/or decompression, performing a concentration process, and heating and drying a remained organic component, trace component and the like. Alternatively, a method like a spray dry technique can be used. However, heating or drying for an extended period at high temperature, for example, at 200° C. or higher is preferably avoided, for preventing the pyrolysis of the silicone rubber component.

When the silicone rubber particles according to the present invention are used in cosmetic applications, they desirably have a particle size of 100 μm or less. A particle size greater than 100 μm causes the size of fine particles to reach the extent of being recognizable by the sense of touch, and therefore is not preferable in terms of the impression from use.

The present invention will be described by way of examples. It is noted that the present invention is not limited by these examples. Silicone rubber particle-dispersed emulsions in examples and comparative examples were prepared as described below. The silicone rubber particle-dispersed emulsions obtained were evaluated for storage stability, water dispersibility, and senses of touch by the following methods. The formulation amounts of the examples and comparative examples are indicated in Table 1, and the evaluation results are indicated in Table 2.

<Storage Stability Test>

Into a 50 ml tube with threaded closure, 30 g of a prepared silicone rubber particle-dispersed emulsion was poured, and stored at room temperature for one month. Then, the presence or absence of creaming and sedimentation separation was checked.

Evaluation Criteria:

A: Creaming and sedimentation separation were not observed.

B: Tendencies of creaming and sedimentation separation were observed.

C: Creaming and sedimentation separation were observed.

<Water Dispersibility Test>

Into a 50 ml tube with threaded closure, 5 g of a prepared silicone rubber particle-dispersed emulsion was poured, and 20 ml of deionized water was further added. A cap was fitted, and thereafter, the tube was manually shaken 20 times.

The dispersion state after having shaken up was observed, and the water dispersibility was evaluated.

Evaluation Criteria:

A: uniformly dispersed

B: partly dispersed, flock remained

C: not dispersed

<Test for Senses of Touch>

Each of three panelists placed 0.05 g of a prepared silicone rubber particle-dispersed emulsion on the back of a hand, and rubbed the emulsion with an index finger in a circular motion.

The smoothness while rubbing and the loose sense of touch after having rubbed and dried were evaluated.

Evaluation Criteria:

AA: extraordinarily smooth

A: smooth

B: somewhat coarse

C: coarse, residues generated

Example 1

An oil-in-water silicone emulsion 1 according to Example 1 was prepared as below. First, 0.05 parts by mass of an N-acyl amino acid condensate (A) was mixed with 10 parts by mass of water and 4 parts by mass of glycerin. Next, in another container, 58.9 parts by mass of a vinyl group-containing polydimethylsiloxane (I) having a viscosity of 200 mPa·s (25° C.) and each terminal blocked with a dimethyl vinyl silyl group and 1.1 parts by mass of a methyl hydrogen polysiloxane (II) having a viscosity of 65 mPa·s (25° C.), containing an SiH group in the side chain and terminal trimethyl siloxy groups were mixed to prepare a mixed oil in which the number (NA) of alkenyl groups and the number (NH) of hydrogen atoms bonded to a silicon atom satisfied NH/NA=1.2/1. Subsequently, 60 parts by mass of the mixed oil of (I) and (II) were added to the mixed liquid of the N-acyl amino acid condensate, water, and glycerin. The obtained product was stirred at 4,000 rpm using an Ultra-Turrax® T50 Basic Shaft Generator G45M manufactured by IKA for dispersion. Then, the remainder of water was further added. While stirring an oil-in-water silicone emulsion (the emulsion 1) at 200 rpm using a propeller-type stirring blade, 0.4 parts by mass of a platinum-vinylsiloxane complex solution (C) containing 1% by mass of platinum atoms was added. The mixture was stirred for 10 minutes to obtain a silicone rubber particle-dispersed emulsion.

Example 2

A silicone rubber particle-dispersed emulsion was obtained in the same manner as that in Example 1, except that in the emulsion 1 in Example 1, the amount of the N-acyl amino acid condensate was 0.025 parts by mass, the amount of glycerin was 2.0 parts by mass, 2.5 parts by mass of silica particles were further added, and 54.0 parts by mass of a vinyl group-containing polydimethylsiloxane (I) having a viscosity of 1,000 mPa·s (25° C.) and 1.1 parts by mass of the methyl hydrogen polysiloxane (II) were mixed to prepare a mixed oil in which the number (NA) of alkenyl groups and the number (NH) of hydrogen atoms bonded to a silicon atom satisfied NH/NA=1.5/1.

Comparative Example 1

An oil-in-water silicone emulsion (an emulsion 2) was prepared as described in Example 1, except that in the emulsion 1 in Example 1, the N-acyl amino acid condensate and glycerin were replaced with 1.0 part by mass of polyoxyethylene cetyl ether (added ethylene oxide: 13 moles), the amount of the vinyl group-containing polydimethylsiloxane (I) was 67.1 parts by mass, the amount of the methyl hydrogen polysiloxane (II) was 2.9 parts by mass, and the remainder was water. An aqueous dispersion of silicone rubber particles was obtained from the emulsion 2 in the same manner as that in Example 1.

Comparative Example 2

An oil-in-water silicone emulsion (an emulsion 3) was prepared in the same manner as that in Comparative Example 1, except that in the emulsion 2 in Comparative Example 1, the amount of the vinyl group-containing polydimethylsiloxane (I) was 49.0 parts by mass, the amount of the methyl hydrogen polysiloxane (II) was 1.0 part by mass, and the remainder was water. A silicone rubber particle-dispersed emulsion was obtained from the emulsion 3 in the same manner as that in Example 1.

Comparative Example 3

A silicone rubber particle-dispersed emulsion was obtained in the same manner as that in Comparative Example 2, except that in the emulsion 3 in Comparative Example 2, the amount of polyoxyethylene cetyl ether (added ethylene oxide: 13 moles) was 0.1 part by mass, and the remainder was water.

TABLE 1

Formulation amount (unit: parts by mass)

| | Example 1 | Example 2 | Comparative Example 1 | Comparative Example 2 | Comparative Example 3 |
|---|---|---|---|---|---|
| Vinyl group-containing poly-dimethylsiloxane (viscosity: 200 mPa · s (25° C.)) | 58.9 | | 67.1 | 49.0 | 49.0 |
| Vinyl group-containing poly-dimethylsiloxane (viscosity: 1,000 mPa · s (25° C.)) | | 54.0 | | | |
| Methyl hydrogen polysiloxane (viscosity: 65 mPa · s (25° C.)) | 1.1 | 1.1 | 2.9 | 1.0 | 1.0 |
| Silica particle | | 2.5 | | | |
| Glycerin | 4.0 | 2.0 | | | 1.0 |
| Water | 36.0 | 40.5 | 29.0 | 49.5 | 49.9 |
| Total | 100.0 | 100.0 | 100.0 | 100.0 | 100.0 |

TABLE 2

Evaluation result of silicone rubber particle-dispersed emulsion

| | Example 1 | Example 2 | Comparative Example 1 | Comparative Example 2 | Comparative Example 3 |
|---|---|---|---|---|---|
| Storage stability | A | A | A | C | C |
| Dispersibility to water | A | A | C | A | B |
| Sense of touch | A | A | B | B | A |

INDUSTRIAL APPLICABILITY

The manufacturing method of the silicone rubber particle-dispersed emulsion according to the present invention uses the surfactant component in a very small amount. Therefore, the environment and the health are not adversely effected, and the stability of the particles in the emulsion is excellent. Thus, the rubber particles obtained from the emulsion can express the intrinsic characteristics of silicone rubber particles. Accordingly, the manufacturing method is possibly utilized as a manufacturing method for a silicone rubber particle which can be effectively used in the applications of cosmetics, synthetic resin materials and synthetic rubber materials.

The invention claimed is:

1. A method for manufacturing a silicone rubber particle-dispersed emulsion, comprising:
   preparing an oil-in-water emulsion comprising:
   (A) an organic surfactant in an amount of less than 0.1 parts by mass, and
   (B) 20 to 80 parts by mass of an organopolysiloxane composition containing an alkenyl group-containing organopolysiloxane of formula (I) below, and an organohydrogen polysiloxane of formula (II) below, such that 0.05 to 59.05 parts by mass of the organohydrogen polysiloxane (II) are contained relative to 19.95 to 79.95 parts by mass of the alkenyl group-containing organopolysiloxanes (I), wherein
   (I) is an alkenyl group-containing organopolysiloxane having an average formula represented by formula (1) and containing two or more alkenyl groups bonded to a silicon atom in one molecule, $$R^1_a R^2_b SiO_{(4-a-b)/2} \quad (1)$$

where
   $R^1$ is a monovalent hydrocarbon group which is the same or different and which does not contain an aliphatically unsaturated group,
   $R^2$ is an alkenyl group,
   a is 0.999 to 2.999,
   b is 0.001 to 2, and
   a+b is 1 to 3;
   (II) is an organohydrogen polysiloxane having an average formula represented by formula (2) and containing two or more hydrogen atoms bonded to a silicon atom in one molecule, $$R^3_c H_d SiO_{(4-c-d)/2} \quad (2)$$

where
   $R^3$ is a monovalent hydrocarbon group which is the same or different and which does not contain an aliphatically unsaturated group,
   c is 0.999 to 2.999,
   d is 0.001 to 2, and
   c+d is 1 to 3; and
   adding, to the resulting oil-in-water emulsion, (C), a platinum group metal-containing addition catalyst in an amount of 1 to 5,000 ppm relative to the total amount of the components (I) and (II), and wherein the component (A) comprises 0.01 to 0.09 parts by mass of an N-acyl amino acid condensate of formula (3),

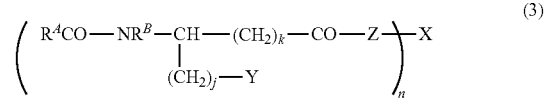

where
   $R^A$ is a hydrocarbon group having 1 to 23 carbon atoms,
   $R^B$ is a hydrogen atom or a hydrocarbon group having 1 to 3 carbon atoms, and Y is a carboxyl group, a sulfonic acid group, a sulfuric acid ester group, a phosphoric acid ester group, or a salt thereof, X is a group for condensing the N-acyl amino acid derivative, Z is —NR'—, where R' is a hydrogen atom or a hydrocarbon group having 1 to 10 carbon atoms, —O—, or —S—, and j and k are each any of 0, 1 and 2, and are not simultaneously 0, and n is 2 or more.

2. A silicone rubber particle-dispersed emulsion prepared by the method comprising:
preparing an oil-in-water emulsion comprising:
(A) an organic surfactant in an amount of less than 0.1 parts by mass, and
(B) 20 to 80 parts by mass of an organopolysiloxane composition containing an alkenyl group-containing organopolysiloxane of formula (I) below, and an organohydrogen polysiloxane of formula (II) below, such that 0.05 to 59.05 parts by mass of the organohydrogen polysiloxane (II) are contained relative to 19.95 to 79.95 parts by mass of the alkenyl group-containing organopolysiloxanes (I), wherein (I) is an alkenyl group-containing organopolysiloxane having an average formula represented by formula (1) and containing two or more alkenyl groups bonded to a silicon atom in one molecule,

where $R^1$ is a monovalent hydrocarbon group which is the same or different and which does not contain an aliphatically unsaturated group, $R^2$ is an alkenyl group, a is 0.999 to 2.999, b is 0.001 to 2, and a+b is 1 to 3;

(II) is an organohydrogen polysiloxane having an average formula represented by formula (2) and containing two or more hydrogen atoms bonded to a silicon atom in one molecule,

where $R^3$ is a monovalent hydrocarbon group which is the same or different and which does not contain an aliphatically unsaturated group, c is 0.999 to 2.999, d is 0.001 to 2, and c+d is 1 to 3; and adding, to the resulting oil-in-water emulsion, (C), a platinum group metal-containing addition catalyst in an amount of 1 to 5,000 ppm relative to the total amount of the components (I) and (II), and wherein the component (A) comprises 0.01 to 0.09 parts by mass of an N-acyl amino acid condensate of formula (3),

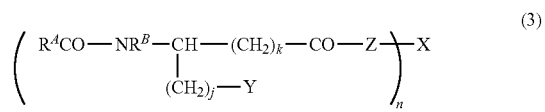

where $R^A$ is a hydrocarbon group having 1 to 23 carbon atoms, $R^B$ is a hydrogen atom or a hydrocarbon group having 1 to 3 carbon atoms, and Y is a carboxyl group, a sulfonic acid group, a sulfuric acid ester group, a phosphoric acid ester group, or a salt thereof, X is a group for condensing the N-acyl amino acid derivative, Z is —NR'—, where R' is a hydrogen atom or a hydrocarbon group having 1 to 10 carbon atoms, —O—, or —S—, and j and k are each any of 0, 1 and 2, and are not simultaneously 0, and n is 2 or more, and recovering an emulsion comprising silicone rubber particles and the N-acyl amino acid condensate of formula (3).

3. A silicone rubber particle obtained by removing water from the silicone rubber particle-dispersed emulsion of claim 2, the silicone rubber particles comprising, in addition to silicone rubber components, residual N-acyl amino acid condensate of the formula (3).

4. A cosmetic comprising silicone rubber particles of claim 3.

5. A cosmetic comprising a silicone rubber particle-dispersed emulsion of claim 2.

* * * * *